United States Patent [19]
Bennett et al.

[11] Patent Number: 6,019,771
[45] Date of Patent: Feb. 1, 2000

[54] DEVICES AND METHODS FOR MINIMALLY INVASIVE HARVESTING OF A VESSEL ESPECIALLY THE SAPHENOUS VEIN FOR CORONARY BYPASS GRAFTING

[75] Inventors: Brian J. Bennett, Menlo Park; Dwight P. Morejohn, Davis; Ivan Sepetka, Los Altos, all of Calif.

[73] Assignee: Cardiothoracic Systems, Inc., Cupertino, Calif.

[21] Appl. No.: 08/759,102

[22] Filed: Dec. 2, 1996

[51] Int. Cl.⁷ ..................................................... A61B 17/32
[52] U.S. Cl. ............................................. 606/159; 606/170
[58] Field of Search ............................... 606/1, 159, 170, 606/171, 180; 604/22

[56] References Cited

U.S. PATENT DOCUMENTS

| | | |
|---|---|---|
| 3,598,125 | 8/1971 | Cogley . |
| 3,713,533 | 1/1973 | Reimels . |
| 3,788,325 | 1/1974 | Jacobsen . |
| 4,128,099 | 12/1978 | Bauer . |
| 4,261,346 | 4/1981 | Wettermann . |
| 4,408,603 | 10/1983 | Blake, III et al. . |
| 4,493,321 | 1/1985 | Leather . |
| 4,759,348 | 7/1988 | Cawood . |
| 4,799,481 | 1/1989 | Transue et al. . |
| 4,821,718 | 4/1989 | Uldall . |
| 4,997,436 | 3/1991 | Oberlander . |
| 5,190,541 | 3/1993 | Abele et al. . |
| 5,258,006 | 11/1993 | Rydell et al. . |
| 5,281,220 | 1/1994 | Blake, III . |
| 5,320,636 | 6/1994 | Slater . |
| 5,330,471 | 7/1994 | Eggers . |
| 5,331,971 | 7/1994 | Bales et al. . |
| 5,372,601 | 12/1994 | Lary . |
| 5,373,840 | 12/1994 | Knighton . |
| 5,392,789 | 2/1995 | Slater et al. . |
| 5,441,510 | 8/1995 | Simpson et al. .......................... 606/159 |
| 5,478,351 | 12/1995 | Meade et al. . |
| 5,695,514 | 12/1997 | Chin ......................................... 606/159 |
| 5,759,150 | 6/1998 | Konoo et al. ............................ 606/159 |

OTHER PUBLICATIONS

"An Improved Technique for Long Saphenous Vein Harvesting for Coronary Revascularization," W. Meldrum–Hanna, F.R.A.D.S., D. Ross, F.R.A.C.S. *The Annals of Thoracis Surgery*, vol. 42, Jul. 1986, pp. 90–92.

*Primary Examiner*—Michael Buiz
*Assistant Examiner*—William Lewis
*Attorney, Agent, or Firm*—Lyon & Lyon LLP

[57] ABSTRACT

Devices and methods for minimally invasive harvesting of a vessel, especially the saphenous vein for coronary artery bypass grafting, are disclosed which facilitate a minimally invasive vessel harvesting procedure. Generally, an instrument is provided which facilitates introduction of vessel harvesting tools through a minimally invasive incision, and provides the capability to separate the vessel from surrounding tissue while minimizing trauma to the patient and preserving the patency of the vessel. The instrument includes a mechanism for separating the vessel from surrounding tissue and may also include mechanisms for severing side branches from the vessel during the harvesting procedure. In one embodiment, an integrated vessel harvesting assembly is provided which may rotate around a vessel and provides a unitary mechanism for separating the vessel from surrounding tissue and for severing the side branches.

15 Claims, 15 Drawing Sheets

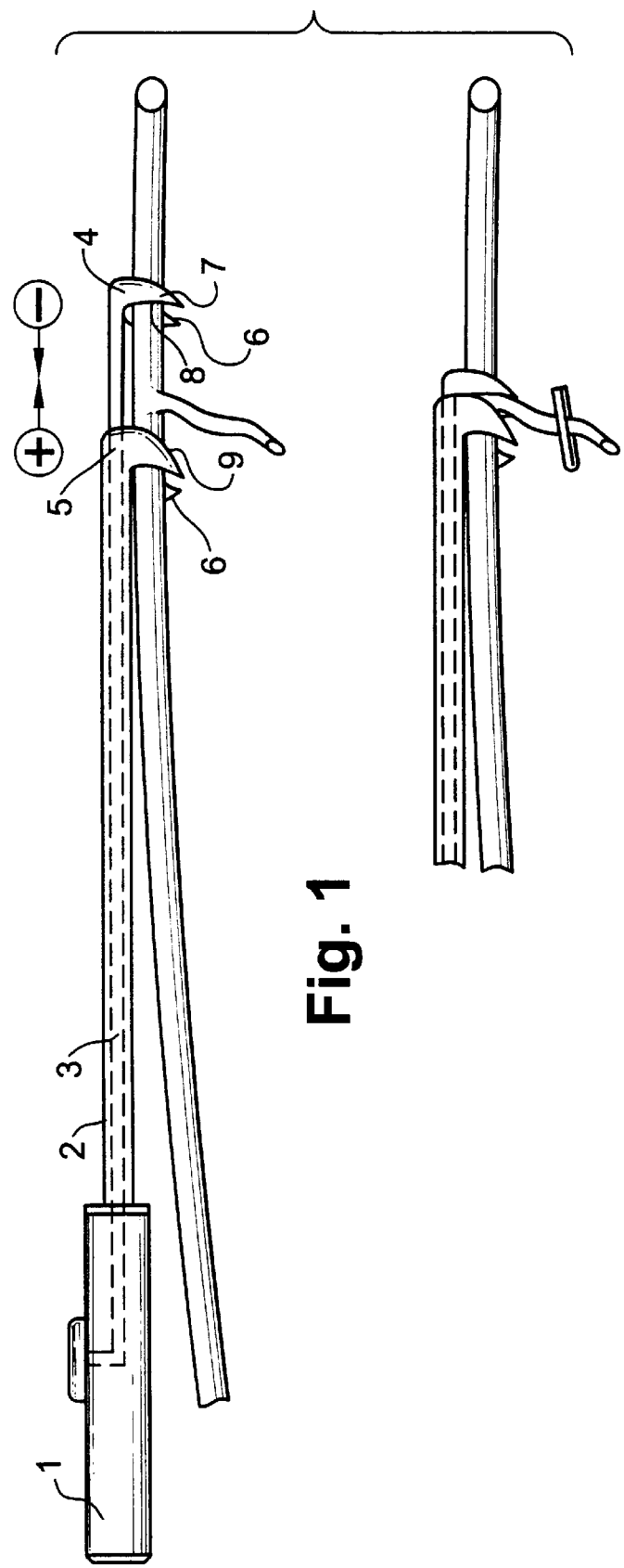

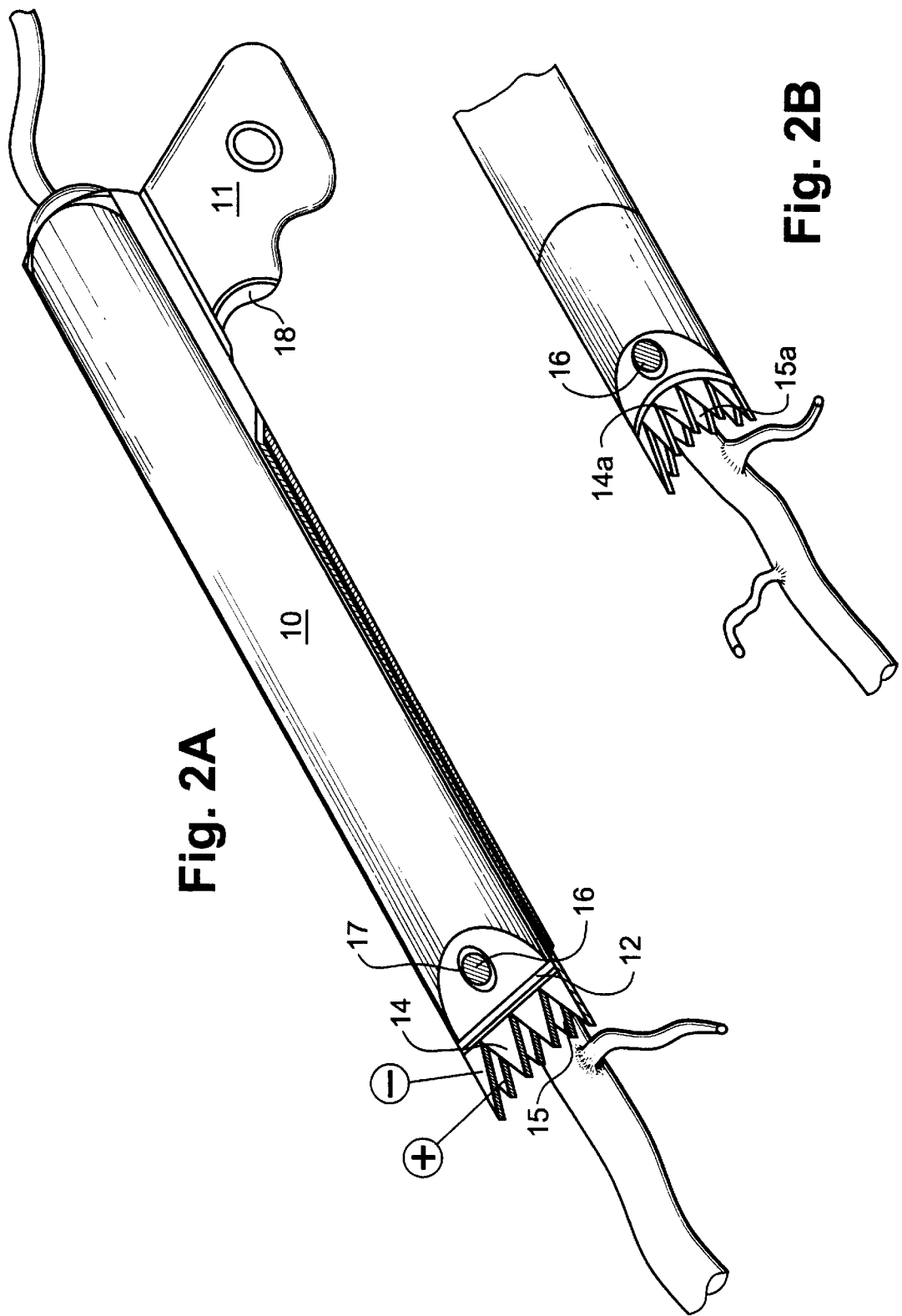

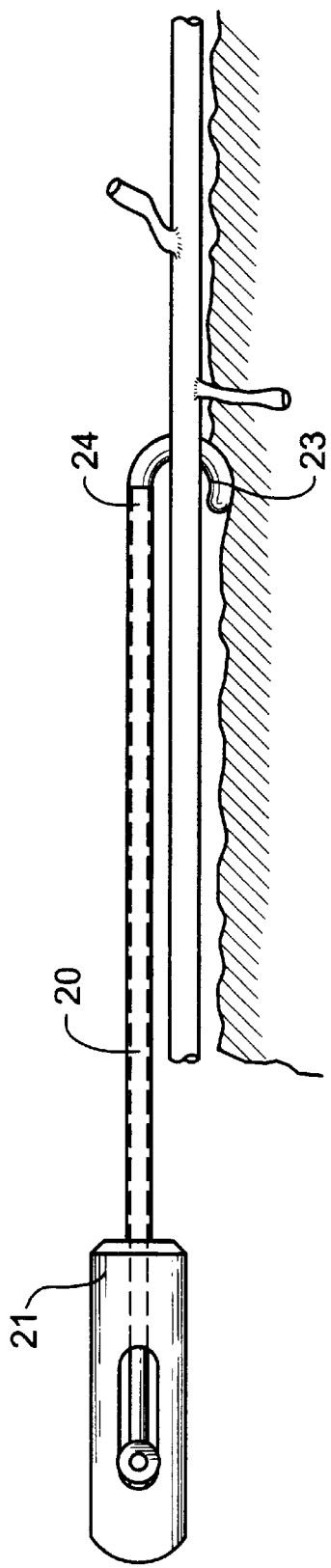
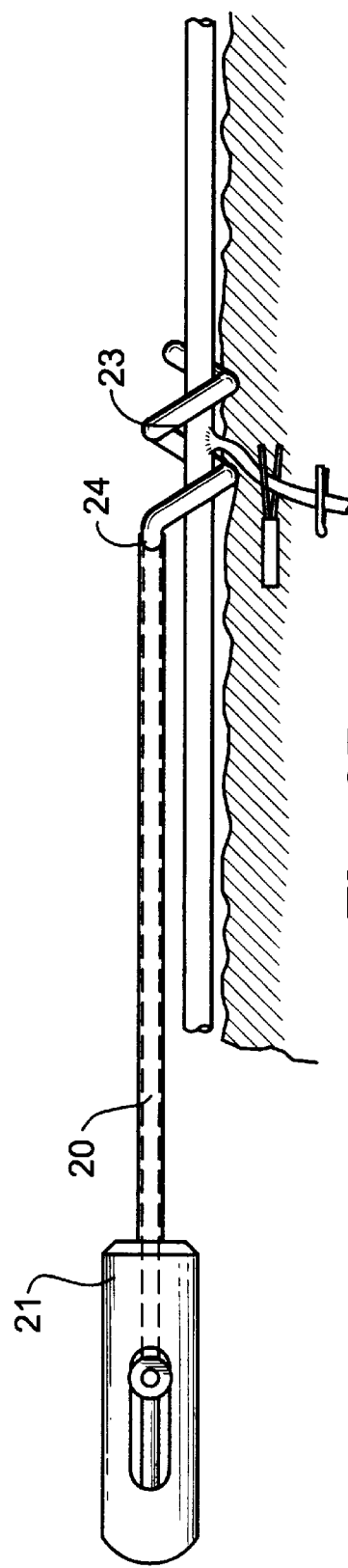

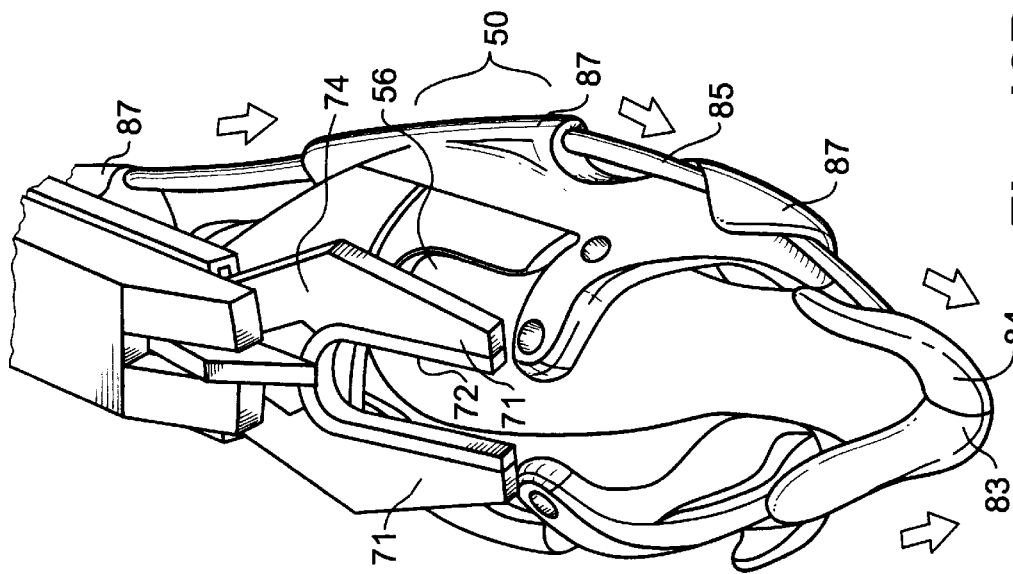
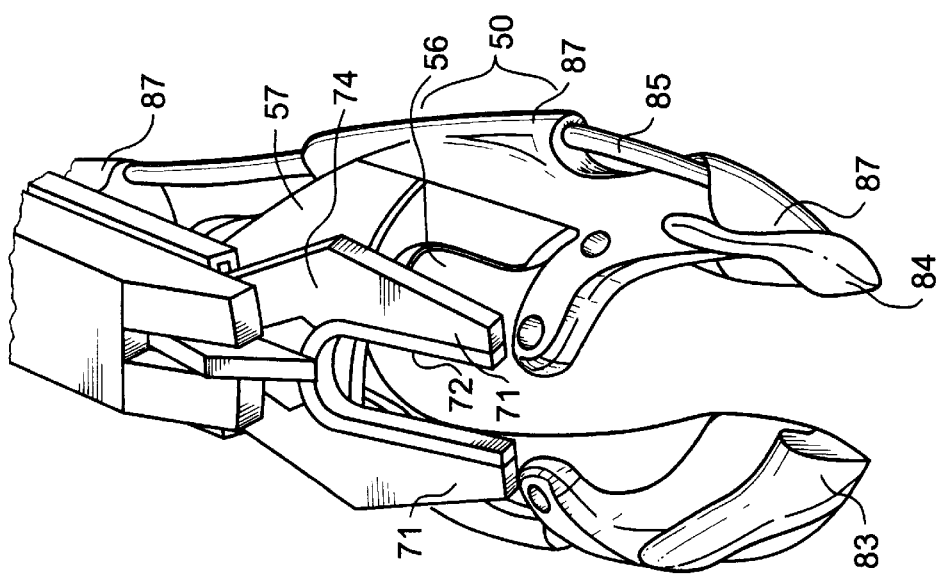

DEVICES AND METHODS FOR MINIMALLY INVASIVE HARVESTING OF A VESSEL ESPECIALLY THE SAPHENOUS VEIN FOR CORONARY BYPASS GRAFTING

Since at least the early 1960's the saphenous vein has been used for coronary artery bypass grafting (CABG). Since that time, coronary revascularization using the saphenous vein has become routine. The use of the saphenous vein is specifically preferred by some surgeons in emergency situations, in patients with poor ventricular function, and in aged patients. Because the saphenous vein is abundant, easy to handle, and has superior flow rates when compared to other available vessels, use of the saphenous vein graft has benefitted many patients undergoing a coronary artery bypass procedure.

However, the surgical procedure used to harvest the saphenous vein prior to its use in the coronary artery bypass graft may be traumatic to the patient. The harvesting procedure also lengthens the overall time and increases the cost of a coronary bypass operation. A long continuous incision down the entire length of the inside of the leg is the standard method to expose and harvest the greater saphenous vein. Major complications of the large wound such as skin loss or infections result in significant morbidity for approximately 1% of patients and frequently cause prolonged hospitalization. Other complications, such as impaired wound healing, saphenous nerve damage, hematomas, prolonged lymphatic drainage, fat necrosis with cellulitis, and chronic edema, can occur at rates exceeding 20% and are particularly costly and traumatic for a patient who has also undergone cardiac surgery. Moreover, many patients who do not suffer major complications still experience lower extremity discomfort lasting 4–6 months after the harvesting procedure. Also, ischemic and/or mechanical injury to the saphenous vein during the harvesting procedure may lead to increased rates of occlusion in the vessel graft in the months and years after the procedure.

To attempt to overcome those problems, less-invasive techniques for harvesting the vein have been developed that reduce the trauma to the patient. Most current less-invasive techniques for dissecting the vessel rely on blunt mechanical force to first create a working space in the tissue surrounding the vein, followed by introducing tools for harvesting the vein through a smaller number of discrete incisions. Additional vessel harvesting tools can be introduced through these smaller incision(s) to permit separating the vein from the surrounding tissue and to separate side branches of the vessel. However, even where these less invasive techniques reduce the overall length of the incision, the trauma to the vessel, the surrounding tissue, and the patient can be severe. In particular, the harvesting procedure itself may actually be lengthened and the trauma to the vessel potentially increased by the less invasive techniques, in part because a number of tools must be introduced through the incision(s) and frequently exchanged for cleaning or to provide functions at the site of the harvesting procedure. The goal of the present invention is to further reduce the trauma to the patient by providing the capability to more rapidly and less traumatically harvest the vein by detaching the vein from surrounding tissue on all sides together with ligating side branches in a more expeditious procedure that reduces or eliminates the need to frequently exchange instruments during the procedure.

SUMMARY OF THE INVENTION

The use of a minimally invasive harvesting procedure and specially designed devices which minimize the trauma to the patient reduces the chances for infection in the wound, maintains tissue perfusion in surrounding tissues, maintains body temperature and fluid volume during surgery, and reduces the overall length of the harvesting procedure. The minimally invasive procedures disclosed herein also enhance the ability to remove an intact and undamaged length of the vessel while minimizing the degree of surgical dissection and trauma to the patient.

In addition to separating the vessel from the surrounding tissue, the saphenous vein typically has numerous side branches which must be separated from the major vein by being severed and secured to permit removal of the vein and to eliminate excess bleeding. Certain embodiments of the invention also provide the ability to separate side branches by cauterization, thereby avoiding the additional trauma and time necessary to separate by the side branches from the major vessel inserting additional tools to mechanically sever the side branches and to secure the side branches by applying clips, staples, sutures or other mechanical fasteners. The harvesting procedure may be continuous without the need to interrupt the procedure to clean the harvesting tools and the need to switch from one tool to another is reduced or eliminated.

In another embodiment, the saphenous vein is separated from the surrounding tissue by an advancing memory coil that extends from within a housing. The coil is extended to partially or completely surround the segment of the vein progressively down the length of the leg, thereby allowing location and securing of the side branches with separate tools while the vein is protected by the advancing coil. Additionally, in this embodiment, the coil can be cleaned by retraction into the housing. In certain embodiments of the invention, the advancing coil may be provided in configurations which facilitate location and separation of the side branches in a continuous procedure without the necessity of introducing additional tools.

Also, the device of the invention may comprise or include an integrated vessel harvesting assembly which severs, ligates, or separates the side vessels using a single instrument. Moreover, the assembly may include the capability to sever and secure the end of the major vessel by remote manipulation of the vessel to within the mechanism used to separate the side branches.

DESCRIPTION OF FIGURES

FIG. 1 is a basic scissors mechanism having, in this example, two cooperating blade members where the more distal blade member separates a vessel from the surrounding tissue, and where the blade members can used together to sever side branches of a vessel by positioning the side branch between the two blade members.

FIGS. 2A and 2B are vessel dissectors having a housing with a handle at one end for remote actuation of a scissor mechanism at the distal end and a scope at the distal end for viewing minimally invasive vessel harvesting procedure. FIG. 2B shows an alternate embodiment for the scissor blade members.

FIG. 3A–B are an embodiment of the invention having an extendable coil which may be actuated by a handle and which may be substantially contained within a housing. The coil is preferably a memory metal having a predetermined configuration and which may extend to partially or completely surround the vessel during the harvesting procedure.

FIGS. 12A–D is a fixture for remote positioning of a portion of the saphenous vein to be clipped or severed within the mechanism of the integrated assembly used to separate the major vessel side branches.

DETAILED DESCRIPTION OF THE INVENTION

Figure 4A:
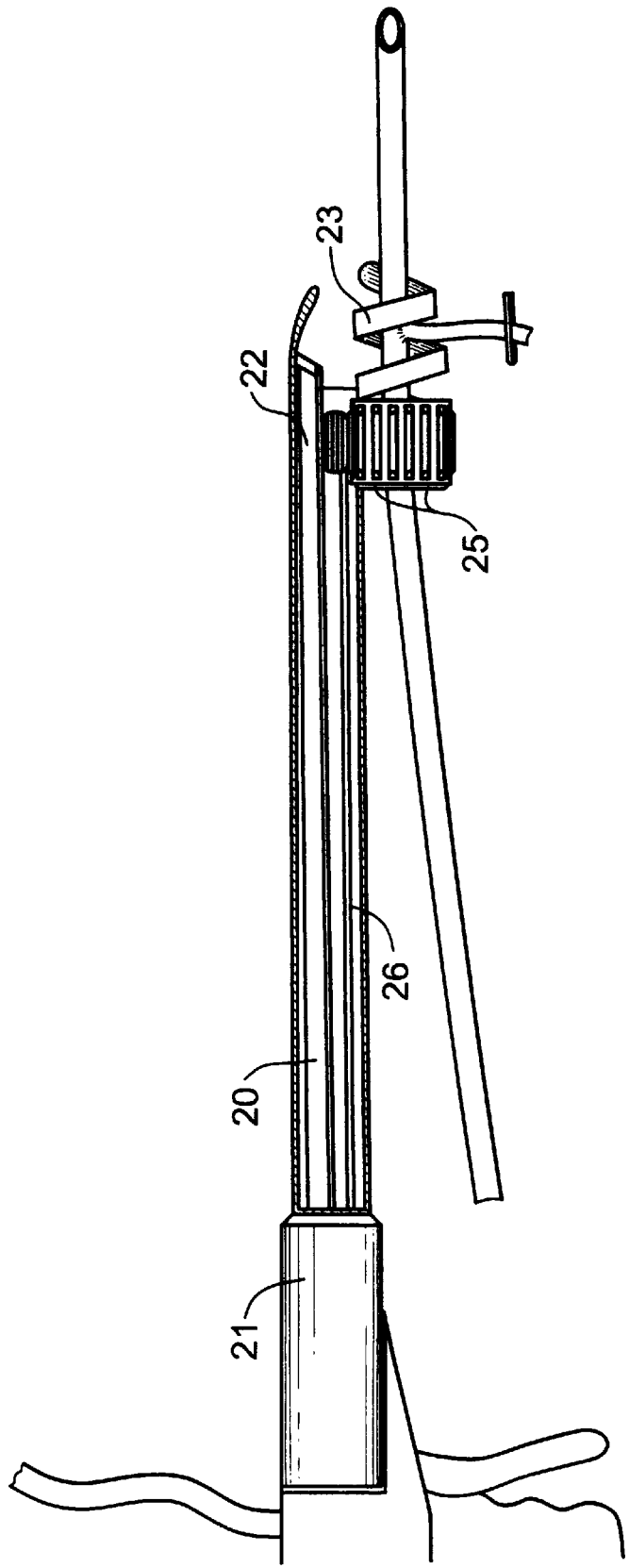
FIGS. 4A–B are an embodiment of the invention having a harvesting coil operably associated with a gear mechanism which is actuated by the operator to rotate the coil progressively around and over the vessel to be harvested. In some embodiments, the coil may have variable spacing between successive coils and cutting edges which may be bipolar to facilitate a continuous harvesting procedure.

Although the precise physiology may vary from patient to patient, the greater saphenous vein generally runs the length of the inner side of the leg in close association with the saphenous nerve and terminates at the groin, where it enters the femoral vein. Prior to harvesting the saphenous vein for a coronary artery bypass procedure, the right or left greater saphenous vein is chosen for removal following a preoperative examination of the legs of the patient. The first priority of the nurse, medical practitioner, or physician performing the saphenous vein harvesting procedure is to obtain an adequate length of saphenous vein for the particular bypass procedure to be performed. For example, the total vein length that is required is determined by the number of coronary artery bypasses to be performed and whether one or both internal mammary arteries will be used as grafts. A minimum length of 6 to 8 inches of saphenous vein is harvested for each bypass graft. When adequate segments of a greater saphenous vein cannot be found, the lesser saphenous vein may then be used if it proves of adequate diameter. On rare occasions, suitable segments of vein cannot be found in either leg and another vessel must be found. The cephalic vein can be taken from wrist to shoulder, but its walls are usually thinner than those of those of the leg veins. Ultimately, a target vessel is identified and the harvesting procedure is planned by selecting a segment or segments of a suitable vessel(s) n appropriate length for removal. In the following description, the saphenous vein is used as the example with the understanding that other vessels may be harvested using the devices and procedures of the invention.

Preoperative venous mapping also facilitates a minimally invasive surgical dissection and reduces the incidence of wound complications. The initial incision may be made in the ankle or groin region or above or below the knee. The saphenous vein has a larger diameter in the groin region and is less fragile above the knee than below the knee. However, some physicians and nurses prefer to make the initial incision at the ankle because of the ease in locating the vein, better exposure, less crowded workspace, and decreased chance of wound infection because of the distal location from the groin. The apparatus of this invention are introduced through one, or a small number of discrete incisions in any of these locations and are progressively advanced along the length of the vessel to be harvested.

As the instrument is advanced, the main trunk of the saphenous vein is dissected from the surrounding tissue while each side vessel is carefully located and separated from the major vessel. Side branches occurring within a segment of the vessel to be harvested are separated at a point close to their entry into the main trunk, typically by the application of a suture, staples or surgical clip to secure the vessel and by severing the side vessel. Pursuant to the invention a side branch may also be separated in a single step by cauterization. Before the vein is removed, placement of a marking suture may indicate its longitudinal position. The ends of the harvested vessel are identified and secured prior to removal. The vessel is then removed and placed in a basin of heparinized saline, or other preservative solution, until the coronary bypass anastomoses are performed.

Referring to FIG. 1, a fundamental component of the device of the invention is a scissors mechanism specially adapted for harvesting of a vessel such as the saphenous vein. An exemplary scissor mechanism may be comprised of a handle 1 adapted to be held by the hand which permits manipulation of the scissors mechanism and control of the movement of the mechanism when used along the length of the saphenous vein and when the scissors mechanism is introduced through a minimally invasive incision. Attached near the proximal end, meaning near or at the handle 1 are means for remote actuation of the scissors mechanism such as a plurality of rods 2 or rigid wires 3 running from the handle to the scissors mechanism. At least one of the rods 2 or rigid wires 3 may be affixed to the handle 1 to allow precise positioning. Near the distal end of the instrument, meaning remote from the handle and at the site that the harvesting procedure is performed, the scissors mechanism is comprised of a tool which provides the ability to separate a vessel from surrounding tissue and to selectively make incisions proximate to the distal end of the instrument.

In one embodiment, the scissors mechanism is comprised of two blade members 4, 5 each of which may be generally circular in shape but having an interruption or opening 6 therein such that both of the blade members 4, 5 may be positioned to substantially surround a tubular vessel structure such as the saphenous vein. The first, and most distal, blade member 4 has a leading edge 7 with a smooth surface designed to be advanced along the length of the vessel, i.e., to facilitate separating the saphenous vein from the surrounding tissue. The opposite surface of the first blade member, opposite the leading edge 7, may be a sharpened edge 8 which may be brought into conforming contact with the leading edge 9 of the second, more proximate, blade member 5 which may also have a sharpened edge, thereby forming a functional scissors between the first and second blade members 4, 5. The second, proximate blade member may also have an opening 8 to completely bypass a side branch if a distinct side vessel separation step is desired or if another discrete side vessel ligation tool is used. Preferably, each blade member is attached to a means for remote actuation of the blade members 2, 3, such as a rod, that allows selective positioning of each the blade members relative to one another.

In such a configuration, the distal first blade member 4 is continually advanced along the length of the vein and may be rotated continuously around the entire circumference of the vein permitting complete separation of the vein from the surrounding tissue. Selective movement of each blade member 4, 5 provides the capability to sever the side branches extending at any angle from the major saphenous vein. Thus, pursuant to this embodiment of the invention, the side branches may severed by passing the distal blade member 4 over the segment of the vessel where the side branch exists while rotating the distal blade member 4, allowing the side branch to pass through opening 6, rotating the distal blade member 4 in either direction and then bringing the leading edge 9 of the second blade member 5 into contact with the trailing edge 8 of the first blade member 4. Thus, any tissue structure extending from the side of a vessel may be severed by positioning the structure between the blade members 4, 5 either by rotation of the handle 1, or by independent rotation of the remote actuation means 2, 3 followed by bringing the blade members 4, 5 together or in sufficient proximity to sever the side vessel. The vessel severing function may be enhanced by providing bipolar blade members 4, 5 where opposite electric charges are applied to the respective members. In this fashion, the complete separation of the saphenous vein from the surrounding tissues is achieved by the advancing edge 7 of the first blade member 4, and likewise, severing of a side branch extending in any direction is achieved by selective positioning of the first 4 and second 5 blade members relative to one another and manipulation of the blade members to sever the structure positioned therebetween.

The scissor mechanism for separating the saphenous vein from the surrounding tissue may be provided in different embodiments consistent with a minimally invasive approach for harvesting the saphenous vein. The scissor mechanism may be integral with an apparatus which provides all the tools necessary to locate, manipulate, and harvest the saphenous vein or, the scissor mechanism may be a separate apparatus which is individually manipulated apart from the remainder of the tools used to harvest the vessel.

Referring to FIG. 2A, a vessel dissector is shown which is particularly useful for harvesting the saphenous vein, but which may also be used to separate other vessels from surrounding tissue pursuant to a minimally invasive surgical procedure. The apparatus is comprised of a housing 10 which has scissor mechanisms at its distal end and a handle 11 at its proximal end. The scissor mechanism is preferably retractable into and out of the housing 10. Although the actual blades may have several configurations, in this embodiment, it is preferred that the scissor mechanism be comprised of a plurality of blades 14, 15 which are parallel and at least one of which moves side-to-side such that the cutting action results from the movement of one or both blades relative to the other due to their orientation being substantially parallel to one another. To enable the use of this apparatus in a minimally invasive environment, a scope 16 may be affixed at the distal end of the housing 10 of the apparatus proximate to the area where the blades 14, 15 are performing the operation of separating the vessel from the surrounding tissue.

The substantial portion of the body of the scope 16, apart from the lens 17 of the scope, may be contained within housing 10 of the apparatus. The housing 10 and the scope 16 disposed therein may be flexible to facilitate following the path of a vessel through the surrounding tissue. The blade members 14, 15 which comprise the scissors mechanism are retractable into the housing 10 of the apparatus by traversing a cleaning edge 12 disposed at the distal end of the housing 10 such that when the blade members 14, 15 are withdrawn into the housing 10, the surfaces of the blades 14, 15 are effectively cleaned by the cleaning edge 12 which removes excess tissue or other such debris. The scissor mechanism may also be made bipolar by having opposite electrical charges imposed on the respective blade members 14, 15. The handle 11 also has means 18 for remotely activating the motion of the blade members 14, 15 such as a switch or trigger for activation of the scissors mechanism.

Referring to FIG. 2B, in an embodiment preferred for harvesting a vessel such as the saphenous vein, the configuration of the blade members 14a, 15a, may be altered to facilitate dissection of a vessel which has substantially tubular or cylindrical regions which must be separated from tissue which surrounds the vessel on all sides. In this embodiment, a pair of curved blade members 14a, 15a are provided as in the above example, such that the blade members 14a, 15a move relative to one another in a substantially equivalent arc such that the cutting mechanism provides an arcuate rather than a linear pathway to separate the vessel from the surrounding tissue. This embodiment, as with the embodiment of FIG. 1, readily provides the ability to rotate the functional portion of the scissor mechanism throughout a 360° angle. This configuration is also advantageous where side branches of a vessel, as in the saphenous vein, are frequently encountered and a desire exists to avoid severing the side branches during the process of dissecting the vessel from the surrounding tissue. In this embodiment, the entire instrument may be rotated to avoid the side branches until a subsequent procedure when the side branches are separated.

Referring to FIG. 3A and 3B, an alternate means for separating a vessel such as the saphenous vein from surrounding tissue may be provided by a coil 23 which wraps completely around the vessel, by turning an entire rotation through 360° to surround the vessel, or by wrapping around only a portion of the vessel at any one time. The coil 23 is contained in a housing 20 which is affixed to a handle 21. The coil 23 may be entirely contained within housing 20 but may be actuated from handle 21 to extend from an opening 24 in the distal portion of housing 20. The coil 23 can be extended, or introduced around the vein, at any required angle and can be turned continuously by extending the coil 23 or by manipulating the handle 21. By this process, the vein is progressively separated from the surrounding tissue progressively along its length. Preferably, the coil 23 is a conformable memory metal, such as the brand Nitinol, with a predetermined helical shape of a coil minimally larger than the diameter of the target vessel. Also, the coil 23 can be constructed such that a portion of the coil contains a cutting edge 24 or bipolar electrode to facilitate more aggressive separation of the vein from surrounding tissue.

The coil configuration of the invention is particularly useful for a minimally invasive procedure whereby the coil 23 is further advanced, i.e., for several helical turns, such that the coil 23 completely surrounds a length of the saphenous vein as shown in FIG. 3B. By continually advancing the coil 23 along the length of the saphenous vein and then manipulating the instrument to cause the extended coil 23 to separate the vein from the surrounding tissue, a continuous harvesting procedure is provided whereby the saphenous vein is readily separated from the surrounding tissue and the side branches of the saphenous vein are simultaneously located. Once a side branch is located, separate tools may introduced next to the coil 23 to separate the side branch, i.e., to apply clips or sutures to secure the side branch, followed by scissors to sever the side branch. An added benefit of positioning the coil 23 to surround the saphenous vein is that the coil 23 protects the vein during manipulation of tools such as the scissors and suture or clip appliers used to separate the side branches.

An additional advantage of a retractable coil 23 embodiment is that the coil 23 itself can be cleaned by withdrawing the coil 23 into the housing 20 whereby any tissue or other debris will be removed against the edge of the opening 24 at the distal end of housing 20. Thus, the distal end of the tool, and the coil 23 itself, are essentially self-cleaning and the length of the saphenous vein can be harvested without interrupting the procedure to remove the tool from the minimally invasive incision for cleaning purposes.

Referring to FIG. 4A, an embodiment of the apparatus of the invention having an extendable coil 23 is shown in cross-section. This embodiment has an expanded housing 20 containing a gear mechanism 25 to progressively rotate and extend the coil 23 over and around the saphenous vein. The gear mechanism 25 is driven by a driving shaft 26 contained within the housing 20 of the device. Also shown is a scope 22 whose lens is located at the distal end of the device, proximate to the area where the coil 23 surrounds the saphenous vein. As in the above embodiment, the coil 23 may be constructed from a memory metal which is actuated by a means associated with handle 21 to facilitate use of this apparatus in a minimally invasive surgical procedure. As is apparent from the foregoing description, the coil 23 may be positioned either by extending an additional length of coil 23 from the housing 20 or by physically manipulating the entire apparatus by moving the handle 21 relative to the saphenous vein. As with the scissor mechanisms described above, this tool may be integral to a device which facilitates harvesting the saphenous vein through a minimally invasive incision, or may be used separately.

Figure 4B:
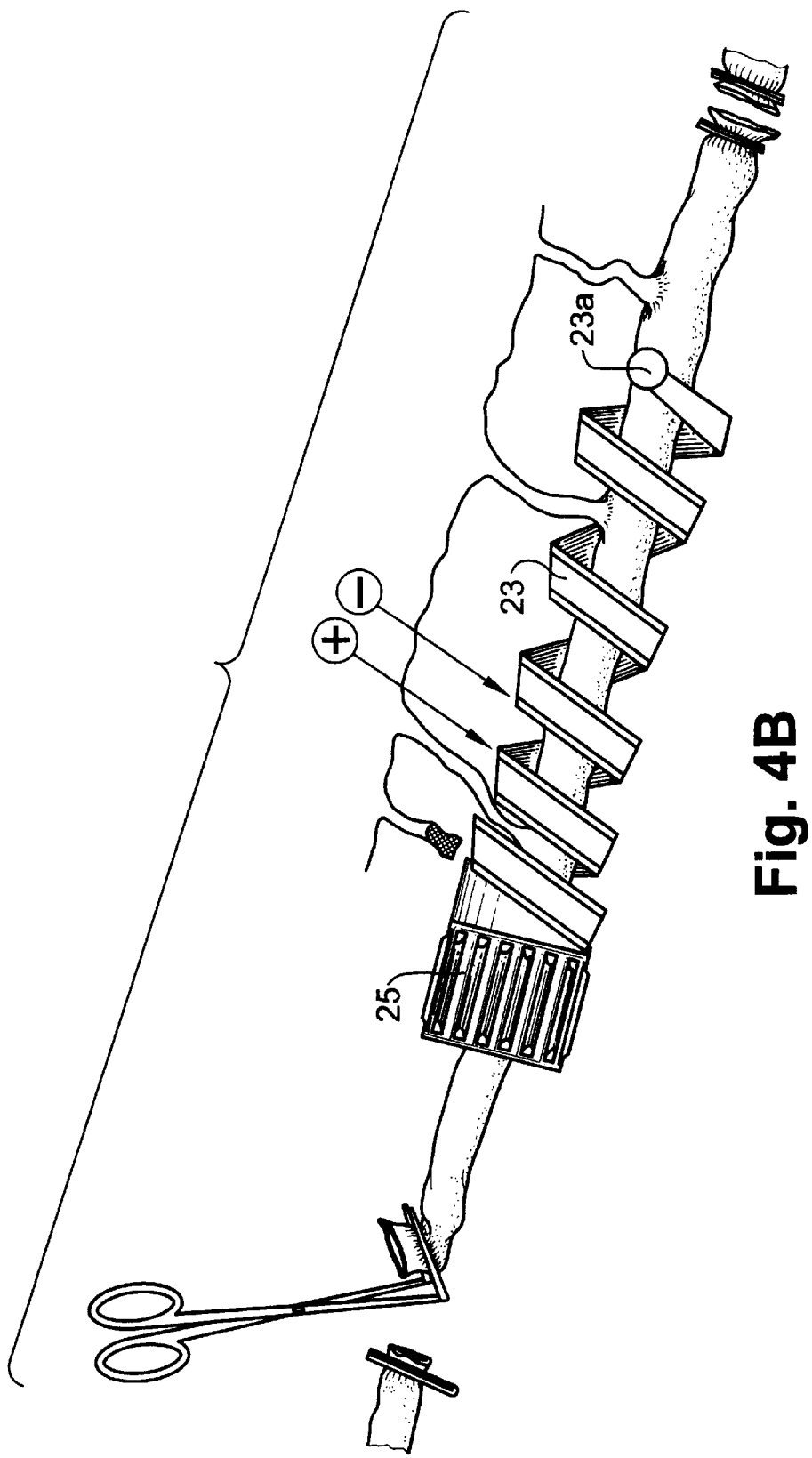

Referring to FIG. 4B, the coil 23 may have variable spacing between the individual coils thereof, provided by the predetermined configuration of the memory metal, such that the spacing between successive coils becomes greater as coil 23 is advanced distally. Thus, the distance between successive coils 23 gradually closes as the coil 23 proximally approaches the handle 21 or the gear mechanism 25. The distal end of the coil 23 may be fused into a circular atraumatic tip 23a to rotate around and to be guided by the vessel. As the coil 23 advances, the major vessel is separated from the surrounding tissue and the side branches are drawn into the decreasing space between the edges of the coil 23 as the distance between the successive coils 23 decreases and the side branch moves proximally to the handle of the instrument. The coil 23 may have sharpened or bipolar edges to sever, secure, or separate the side branches of the vessel as the coil 23 is advanced. To draw the vessel through the advancing coil 23, one end may be severed and tension exerted on the vessel in a direction opposite to the direction of the advancing coil 23 such as by conventional forceps.

Figure 5:
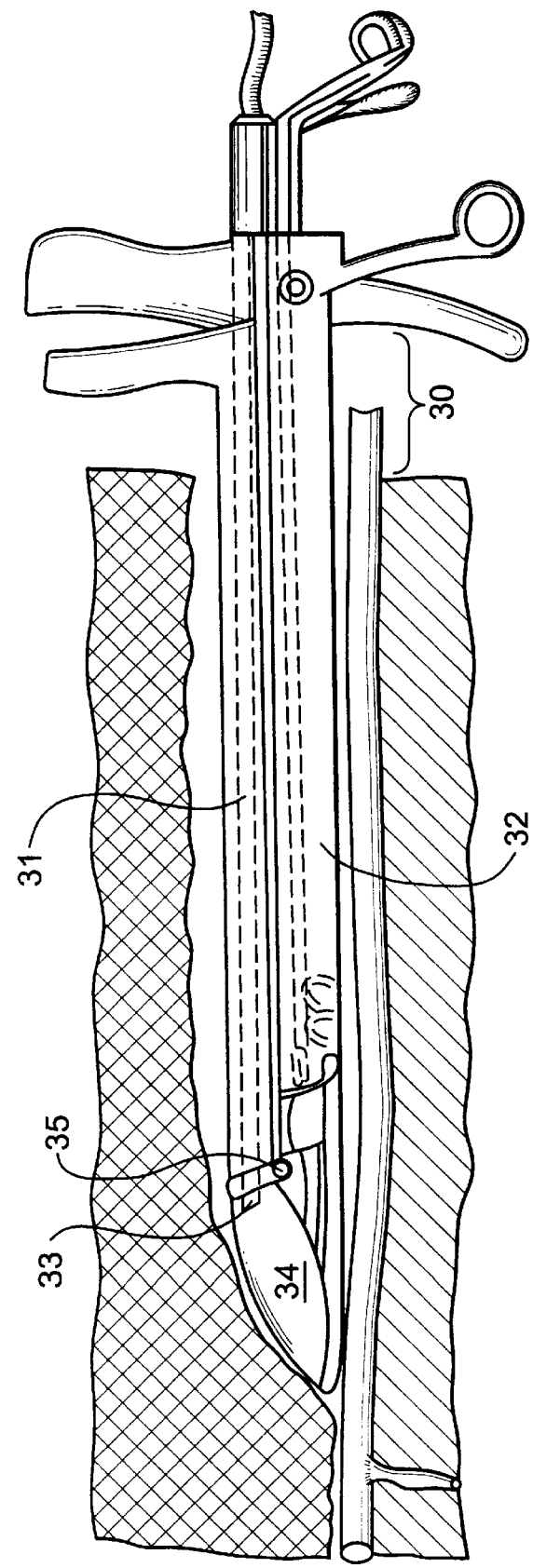
FIG. 5 is a vessel harvesting system having a plurality of shafts which may be inserted through a minimally invasive incision and provides a shield at the most distal end of the instrument to protect the vessel and to provide a protected surgical field for the manipulation of additional instruments during a vessel harvesting procedure.

Referring to FIG. 5, an embodiment of the invention is shown which is comprised of several harvesting tools incorporated into a complete and interrelated system to enable minimally invasive saphenous vein harvesting within a single instrument. The integrated system is generally comprised of an instrument 30 which incorporates a plurality of shafts to enable introducing several discrete instruments or tools to the distal end of the instrument 30. As with each of the embodiments disclosed herein, the instrument 30 may be provided with surgical lights, suction, irrigation, or related functions to facilitate the procedure. Preferably such functions are provided by means disposed within the housing of the instrument 30. Additionally, the application of focused or directed air pressure may be used to separate the vessel from the surrounding tissue. The instrument 30 is introduced through a minimally invasive incision and progressively advanced along the length of the saphenous vein. The instrument 30 is constructed such that each of the discrete vein harvesting tools or other instruments may be introduced through the body of instrument 30 from the proximal end of the instrument 30 which extends out from the minimally invasive incision. Where the associated tools and apparatus permit, the instrument 30 and related tools may be flexible. Each such instrument or tool is positioned at the distal end of instrument 30, proximate to the area of the saphenous vein that is being harvested, without causing any additional trauma to the patient. Although the number may vary, the instrument 30 has at least two shafts, an upper shaft 31 and a lower shaft 32. The vessel harvesting tools may be introduced through lower shaft 32 while a surgical scope 33 is preferably introduced through upper shaft 31. At the distal end of instrument 30 is a shield 34 which is encounters and spreads the surrounding tissue along the length of the saphenous vein to expose each segment of the saphenous vein where use of the harvesting tools and other instruments is desired. The overall length of the upper shaft 32 including the shield 34 is greater than that of the lower shaft 32 so that the instruments introduced through lower shaft 31 may operate at a segment of the saphenous vein which is covered by shield 34. The instruments introduced through lower shaft 31 may include a scissors mechanism, a clip applier, suturing instruments, the integrated harvesting assembly described below, or other tools useful for separating the saphenous vein from the surrounding tissue or separating the side branches thereof.

The primary function of the shield 34 is to create a surgical field immediately proximate to the saphenous vein such that the tools introduced through lower shaft 32 may be used to harvest the saphenous vein in a minimally invasive procedure that does not cause additional trauma to the patient each time an additional tool is introduced and which enables rapid introduction of individual tools and rapid and atraumatic switching between different tools or instruments. The entire harvesting procedure is thereby viewed via the scope 33 introduced through upper shaft 31 of the instrument 30. Preferably, the scope 33 remains in a fixed position therein while individual instruments may be sequentially introduced through lower shaft 32 as dictated by the particular needs of the procedure. In one embodiment, the shield 34 may be attached to the upper 31 or to the lower shaft 32 at one or more points at their distal ends by a pivot 35 or hinge or rotating ball joints which allows the shield 34 to move in three dimensions relative to the upper 31 or lower shaft 32 and the target vessel. By moving the shield 34, a larger operating field can be created at any point surrounding a desired portion of the saphenous vein. For example, additional instruments may need to be introduced through instrument 30 at a particular point in the procedure such as where a side branch is encountered. The ability to move the shield 34 as the instrument 30 is advanced progressively along the vein also serves to separate the vessel from the surrounding tissue. Separation of surrounding tissue may also be achieved by providing a rapid vibration mechanism affixed to the shield 34 such that the vibrational motion causes less traumatic dissection of the tissue encountered by the shield 34.

Figure 6:
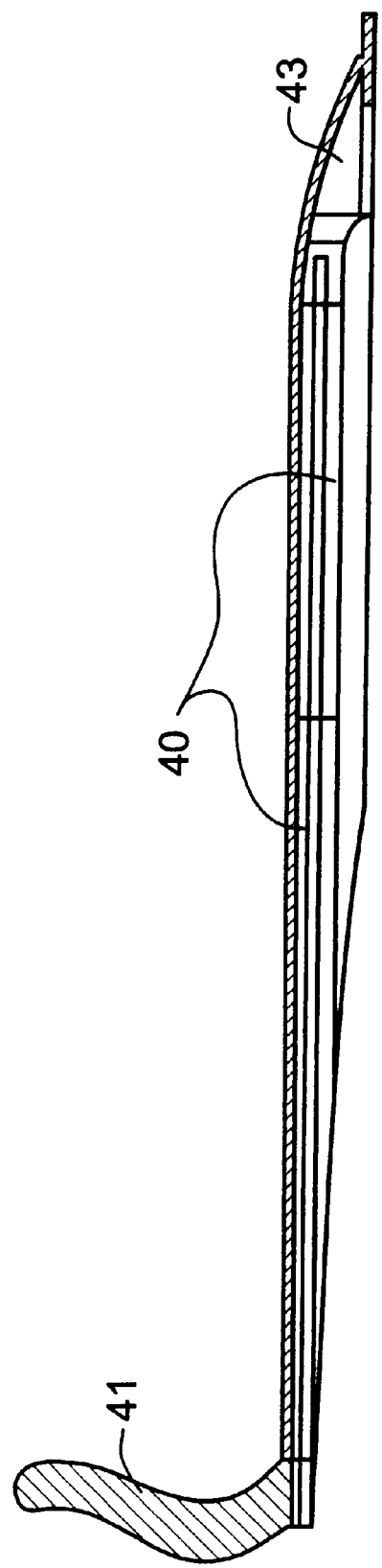
FIG. 6 is the exterior view of an instrument of the invention which provides a unitary shaft through its interior such that the instrument can be positioned by means of a handle at its most proximate end and instruments or tools can be introduced through the body of the instrument to perform a minimally invasive harvesting procedure at its most distal end.

Referring to FIG. 6, an embodiment of the invention is shown which has a housing 40 that runs the length of the instrument and facilitates introducing instruments along its length for minimally invasive harvesting of the saphenous vein. The instrument comprises a handle 41 attached to the housing 40 and adapted to be held by the hand such that the instrument can be positioned along the length of the saphenous vein by manipulating the handle 41. The overall length of the instrument may vary but should have at least the length required to access the most remote portion of the saphenous vein which is accessible through a minimally invasive incision. The exterior of the body of the instrument is smooth to reduce trauma to the surrounding tissue upon insertion and removal of the instrument. The distal end of the instrument has an enlarged nose portion which acts as a shield 43 as the instrument is advanced progressively along the length of the saphenous vein. In a preferred embodiment, the housing 40, which defines the interior of the body of the instrument, is hollow and roughly semicircular in cross-section to facilitate introducing instruments or tools through the housing to the distal portion of the instrument. Within the housing 40 of the instrument, one or more guides may be placed so that additional tools may be introduced through the proximal end of the housing 40 of the instrument and guided along the length of the instrument to reach the portion of the saphenous vein positioned beneath shield 43. The exterior of the housing 40 of the instruments is held in place by friction with the surrounding tissue while the additional tools are introduced through the housing 40.

Figure 7:
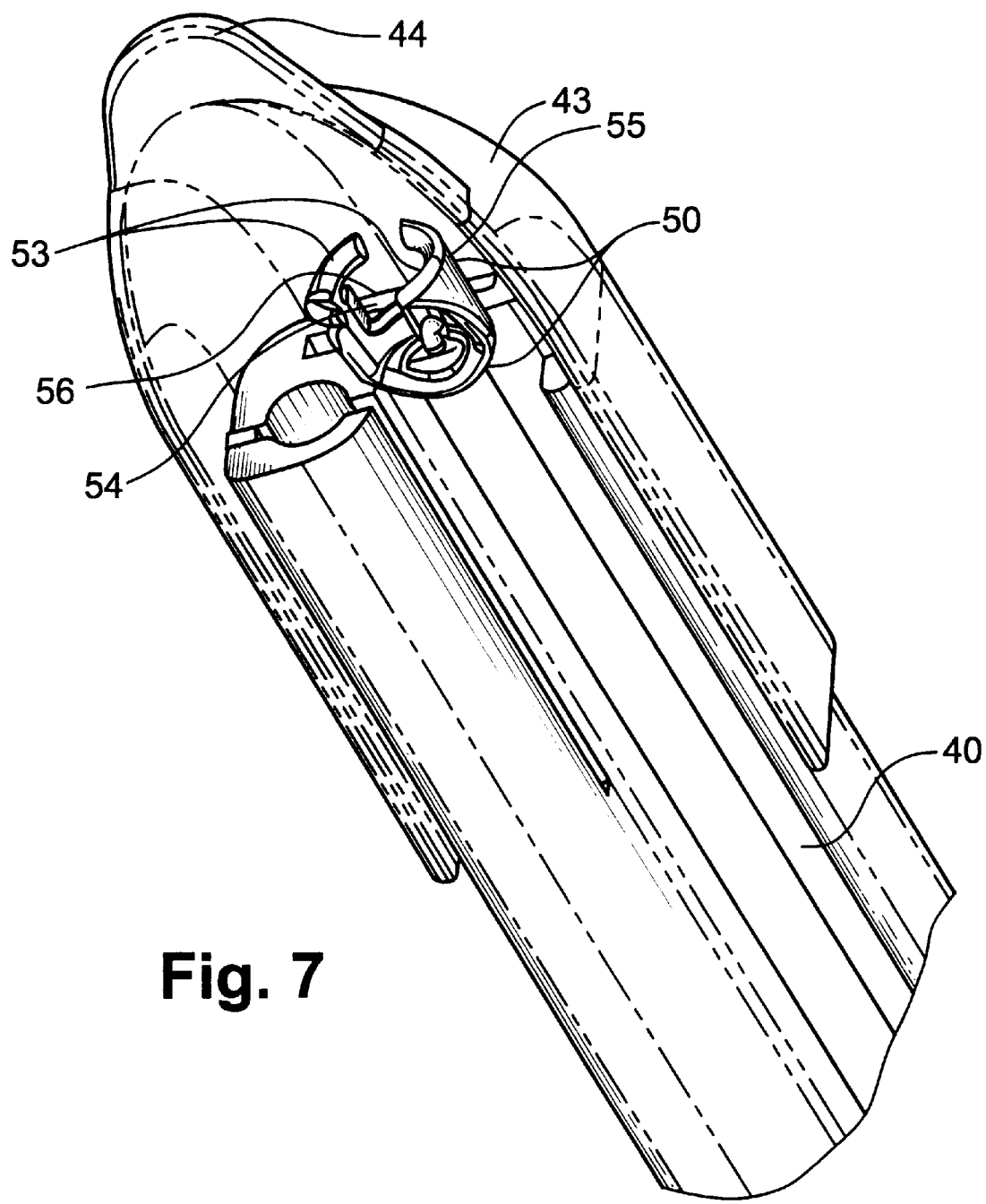
FIG. 7 is a view of the interior of the most distal portion of an instrument, which is preferably of the design of FIG. 6, showing the shield or nose portion of the instrument together with fixtures located inside the most distal portion of the instrument for viewing and performing the harvesting procedure.

Referring to FIG. 7, a bottom view of the shield 43 portion of instrument 40, showing the most distal portion of the housing 40, reveals a fixture for insertion of a scope (not shown) and a preferred configuration of an integrated vessel harvesting assembly 50, having a means for separating side branches of a vessel, positioned to be disposed within the shield 43 portion of the housing 40. In this embodiment, the scope 52 is positioned to view the function of the integrated vessel harvesting assembly, or other instruments or tools operating within the distal end of the housing 40, and is preferably fixed in position so that the harvesting procedure is remotely viewed through the minimally invasive incision. The integrated vessel harvesting assembly 50 is connected to a dedicated handle 51 for activating the various functions of the integrated assembly as described below and as shown in FIG. 9D. The dedicated handle 51 is preferably shaped so that the handle 41 at the proximate end of the housing 40 of the instrument and the dedicated handle 51 which actuates the assembly 50 can be held simultaneously by the hand. The assembly 50 is introduced through the housing 40 of the instrument and is brought into position at the distal end of the instrument proximate to the region of the vessel to be harvested. During the harvesting procedure, the vessel is carefully passed longitudinally within the guide portion of the integrated vessel harvesting assembly 50 such that the integrated assembly 50 may be advanced and rotated about the length of the vessel as it is harvested.

In use, the shield 43 creates a surgical field surrounding the area of tissue which encompasses the saphenous vein. The integrated vessel harvesting assembly 50 then isolates the vessel from the surrounding tissue as the instrument is advanced along the length of the saphenous vein to be harvested without the need to first create a working space followed by exchanging tools to complete the harvesting procedure. Preferably, the shield 43 has a nose portion 44 to facilitate linearly advancing the instrument through the intact tissue surrounding the vessel. By viewing the vessel through a scope 52, the surgical procedure may be monitored while the instrument is advanced along the vessel. The vessel is progressively removed from the surrounding tissue as an advancing edge 53 of the body 55 of the integrated vessel harvesting assembly 50 is advanced along and around the entire length of the vessel. The integrated assembly 50, while substantially surrounding the vessel, is not formed of an unbroken annular structure because it is expected that side branches of the vessel will frequently be encountered along its length, or the assembly may be desired to be removed from about the vessel at some point in the procedure. To avoid the step of removing an intact annular tool from the entire length of the vein, the integrated vessel harvesting assembly has an opening 54 in the body 55 thereof such that the integrated assembly 50 can be completely removed from the saphenous vein at any point and can be rotated to allow side branches to pass through the opening 54 while the integrated assembly 50 continues further along the vessel. Alternatively, at each point where a side branch is encountered, the integrated assembly may be used to separate the side branch from the major vessel, before moving the integrated assembly 50 to harvest other regions of the vessel, by positioning the side branch in an aperture 56 as described in more detail below.

The use of a bipolar charge on the integrated assembly is particularly useful because the side branch may be separated from the major vessel by cauterization in a single step as each side branch is encountered. Where electrocautery is not used, the separation of a side vessel requires both securing the side vessel, for example, by ligation to stop excess flow of blood, and severing the side vessel to permit removing the intact major vessel. Thus, the side branches may be separated by application of clips at each side branch to secure the vessel, followed by the separate step of severing the side vessel. These sequential steps may require sequential insertion and removal of different tools or instruments. Alternatively, the integrated assembly 50 may be entirely provided with a dedicated and integrated clip applier as described below.

Figure 8:
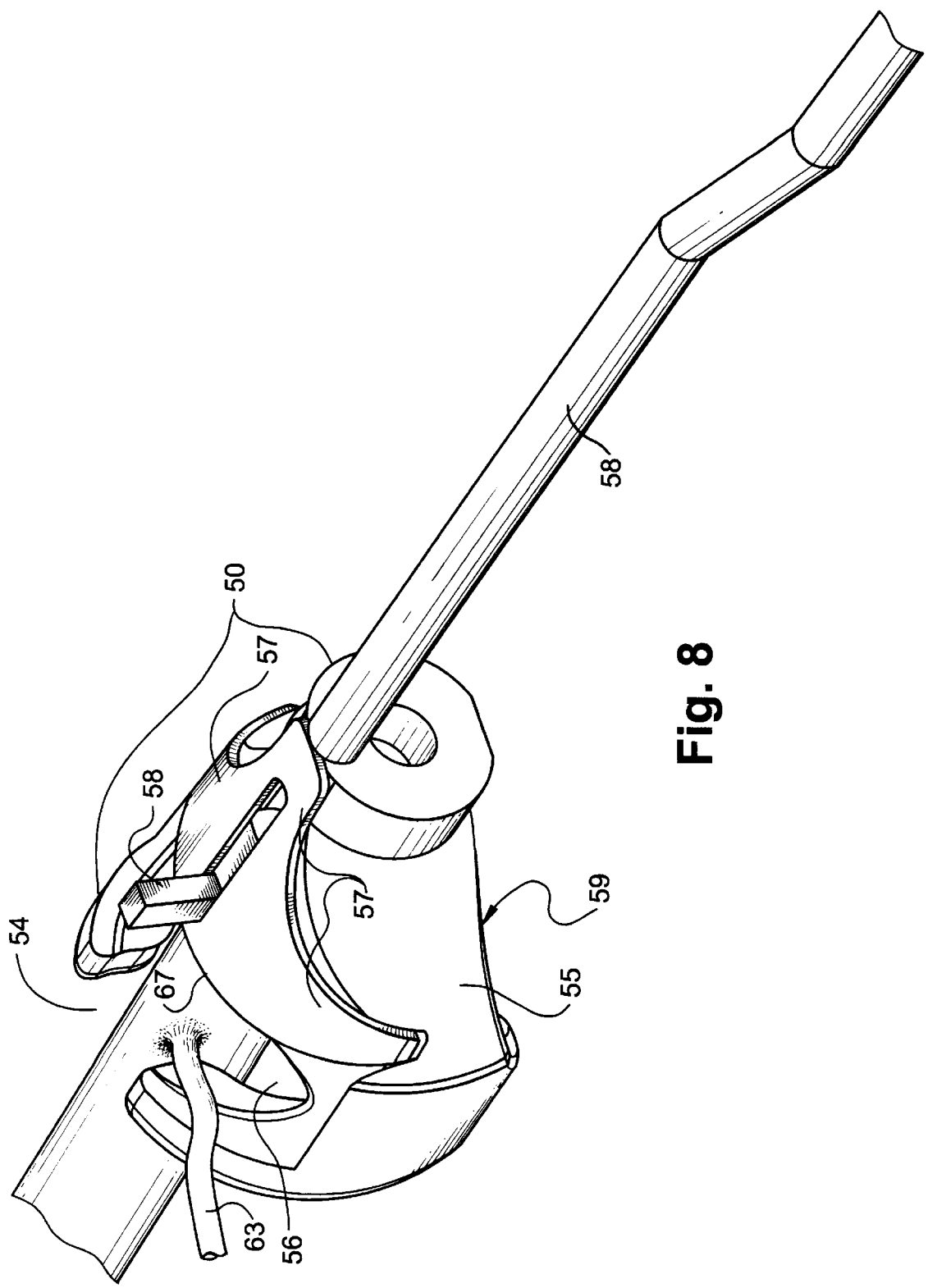
FIG. 8 is an integrated vessel harvesting assembly comprised of a movable blade member, a substantially annular body for positioning of a vessel therein, an advancing edge for separating the vessel from surrounding tissue, and an aperture within the body of the assembly for positioning side vessels to be severed or cauterized.

Referring to FIG. 8, a portion of a vessel such as the saphenous vein is shown disposed within the integrated vessel harvesting assembly 50. A side branch of the saphenous vein is shown having been introduced through the opening 54 in the body 55 of the integrated assembly 50 and the side branch having been positioned, by rotating the entire integrated assembly 50, to be disposed within the aperture 56 of the assembly 50 and proximate to the means for separating a side vessel 63. In one embodiment, the means for separating a side vessel 63 is provided by the sides of the aperture 56 formed in the body 55 of the integrated assembly 50 such as where the aperture 56 has at least one sharpened edge 58 formed therein for severing a vessel within the aperture 56 when the movable blade member 57 encounters the vessel positioned therein.

In a preferred embodiment, the integrated vessel harvesting assembly 50 has a movable blade member 57 operably associated therewith and which moves coaxially with the integrated vessel harvesting assembly to sever structures within the aperture 56 located in the body 55. In this embodiment, the movable blade member 57 is operated by a coaxial means for actuating the movable component 58 such as a rod or rigid wire which may run axially through the housing 40 of an instrument. In the most distal position, the movable blade member 57 essentially covers the aperture 56 formed in the body 55 of the integrated assembly 50 such that structures positioned within the aperture 56 are severed.

Figure 9A:
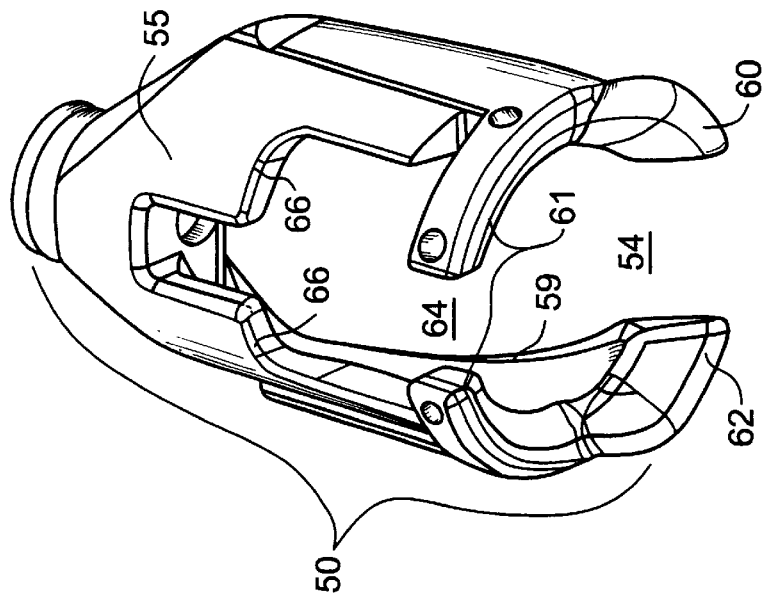
FIGS. 9A–9C are the detail of one component of the integrated vessel harvesting assembly wherein the annular body has at least one advance edge for separating the major vessel from surrounding tissue, a first opening in the body for positioning the vessel therein, and a second opening leading to an aperture to facilitate separating the side vessels.
Figure 9C:
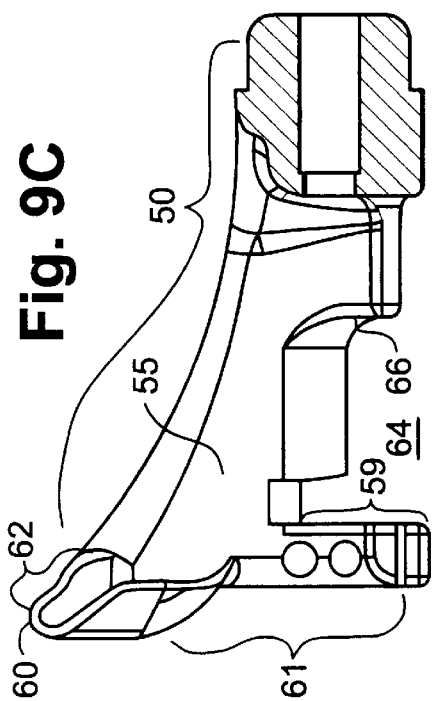
Figure 9B:
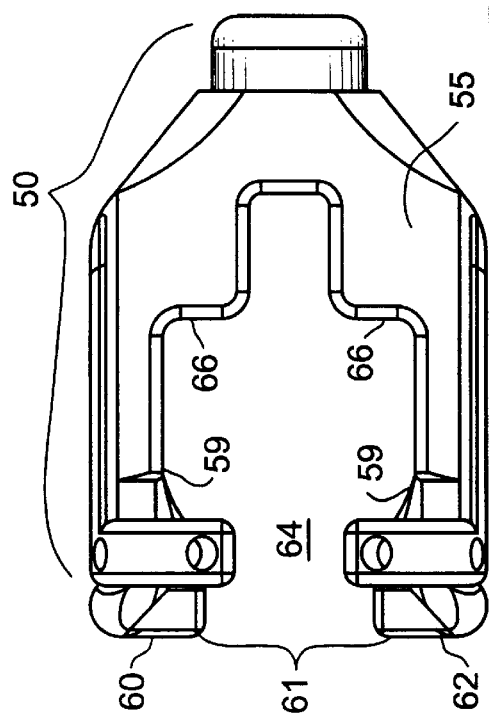
Figure 9D:
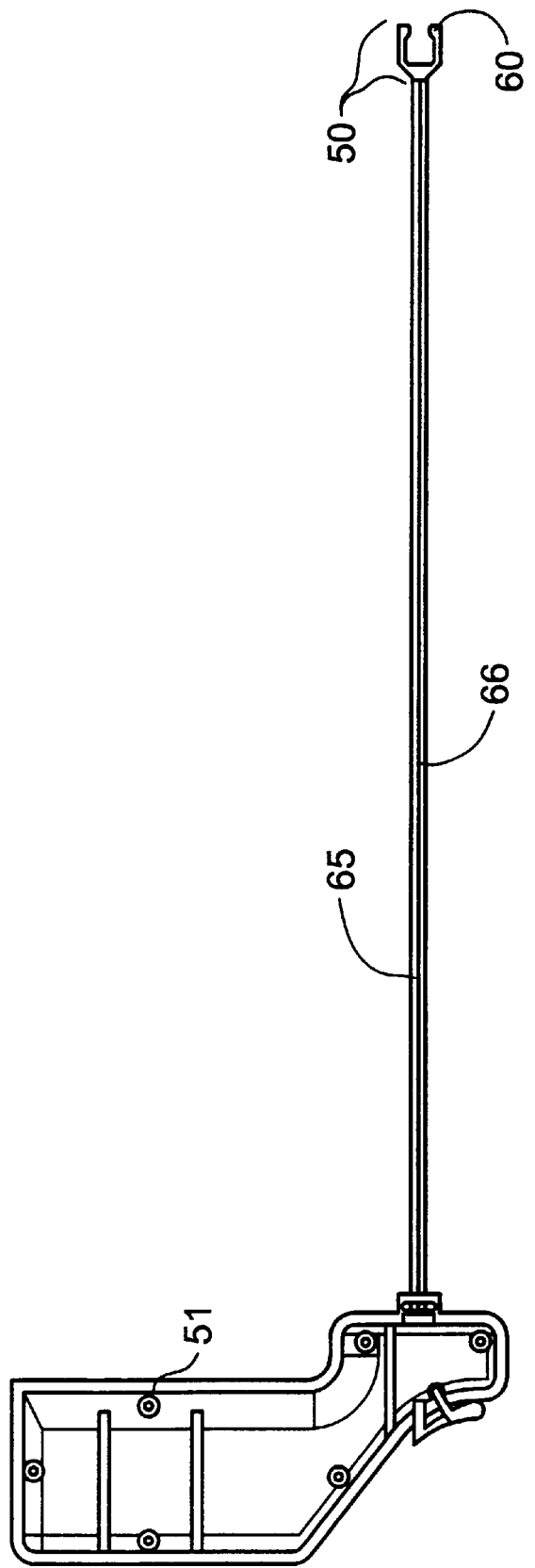
FIG. 9D is the integrated assembly attached to means for rotating and positioning said assembly.

Referring to FIGS. 9A through 9C, a detailed view of the integrated vessel harvesting assembly 50 described above is shown. The body 55 of the integrated vessel harvesting assembly 50 preferably has substantially annular portion 61 and has at least one guide portion 59 formed therein through which the vessel passes during the harvesting procedure. The guide portion 59 is preferably an off-center space passing through the annular body 55 which also facilitates rotating the entire integrated assembly 50 around a vessel positioned in the guide portion 59. A leading edge 60 of the body 55 of the integrated assembly 50 operates to physically divide the vessel from the surrounding tissue. The leading edge 60 should have a narrow but smooth edge to avoid causing trauma to the vessel or the surrounding tissue.

As can be seen in FIG. 9A, the body 55 of the integrated assembly 50 has an annular portion 61 at the most distal end and has a blunt leading edge 60 encompassing at least a portion of the annular portion 61 of the body 55. In a preferred embodiment, the blunt edge 60 has a distally protruding portion 62 to more easily separate the vessel from the surrounding tissue. The body 55 of the integrated assembly 50 also has an opening 54 such that the vessel can be introduced into the guide portion 59 and generally maintained in the annular portion 61 of the body 55. Preferably, the annular portion 61 has at least two openings, the first opening 54 for positioning of the vessel therein, and a second opening 64 providing access, and leading to, the aperture 56 for separating side branches of a vessel.

Referring to FIG. 9D, the entire integrated assembly 50 is secured to a means for positioning and rotating the integrated assembly 65 such as a rod 66 or rigid wire which is attached to the dedicated handle 51 for the device. The means for positioning and rotating the assembly 65 is preferably attached to the most proximate end of the integrated assembly 50 and, as noted above, is attached to the body 55 at a location which is off-center to the annular portion 61 such that the vessel can lie coaxially to the positioning and rotating means 65 and so that the entire assembly 50 can be rotated 360° about the vessel. This configuration also permits ready positioning of side branches through the second opening 64 in the annular portion 61 and passing the side branches into the aperture 56. The movable blade member 57, in a configuration which slides above the aperture 56 of the body 55, may advantageously be used to separate side vessels by both severing and effectively securing the side branches of a vessel simultaneously by providing a bipolar electrical charge between the body 55 of the assembly 50 and the movable blade member 57. In this configuration, the side branches are located, and may be separated by electrocauterization in a single procedure, without the need to introduce additional tools such as suturing mechanisms or clip appliers to ligate the vessel followed by removal of the ligating tool to insert a separate tool to sever the vessel.

Figure 10:
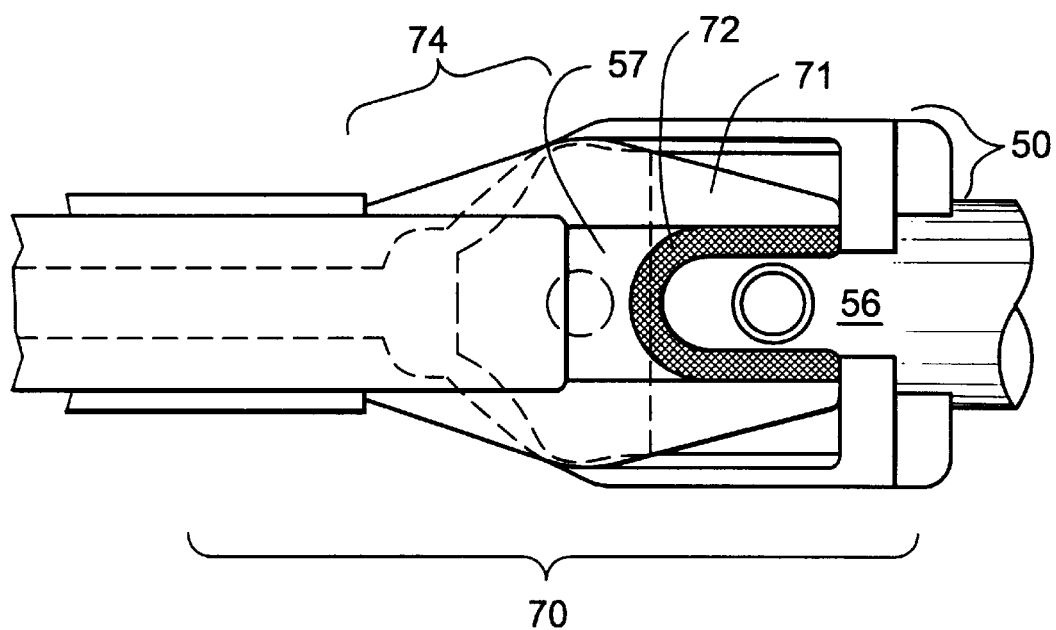
FIG. 10 is the integrated vessel harvesting assembly having an attached clip applier for applying surgical clips to side branches extending from a major vessel.

Referring again to FIG. 8, at either side 66 of the aperture 56, or at the leading edge 67 of the movable blade member 57, or both, may have a knife edge for severing side vessels. In such a configuration the movable blade member 57 and the side 66 of the aperture 56 act like a scissor mechanism to sever vessels positioned within the aperture. Alternatively, to use electrocautery to seal the side vessels, the relative distances and positions of the sides 66 of the aperture 56 and the movable blade member 57 may be altered to provide a limited space therebetween such that when the movable blade member 57 is positioned to engage the aperture 56 a space exists therebetween. Thus, when the movable blade member 57 is positioned in its most distally extended position, a space exists between the movable blade member 57 and the body 55 of the assembly 50 such that the vessel positioned in the space is not immediately severed. Instead, the vessel is first sealed by electrocautery and then separated from the major vessel by the completion of the cauterization or by exerting minimal force to the side branch by manipulating the integrated assembly 50 itself.

Where side branches of the major vessel are not separated by cauterization, the integrated vessel harvesting assembly 50 may include an integrated clip applier 70 that is preferably located proximate to and above the aperture 56 for applying surgical clips to the side vessels. Referring to FIG. 10, the clip applier 70 is comprised of plier grips 71 which engage the surgical clips 72 along each parallel side of the clip. The plier grips 71 are an integral part of a plier mechanism 74 which applies force to the surgical clips 72 to compress the clips 72 to secure and seal a side vessel which has been positioned between the parallel sides of the clip 72. The method of separating the side branch from the major vessel is thus achieved by advancing the integrated assembly 50 along the vessel, introducing a side branch into aperture 56, followed by applying the surgical clip 72 to the side vessel by closing the plier mechanism 74. Once the vessel is clipped, the movable blade member 57 is advanced, and the side vessel is severed, such as between the movable blade member 57 and the side of the aperture 56. The clip applier may be a conventional clip applier modified to be integrated into the assembly of the invention, e.g., U.S. Pat. No. 4,408,603, and may contain a supply of clips such that a new clip 72 is advanced into place as each clip is applied.

Figure 11B:
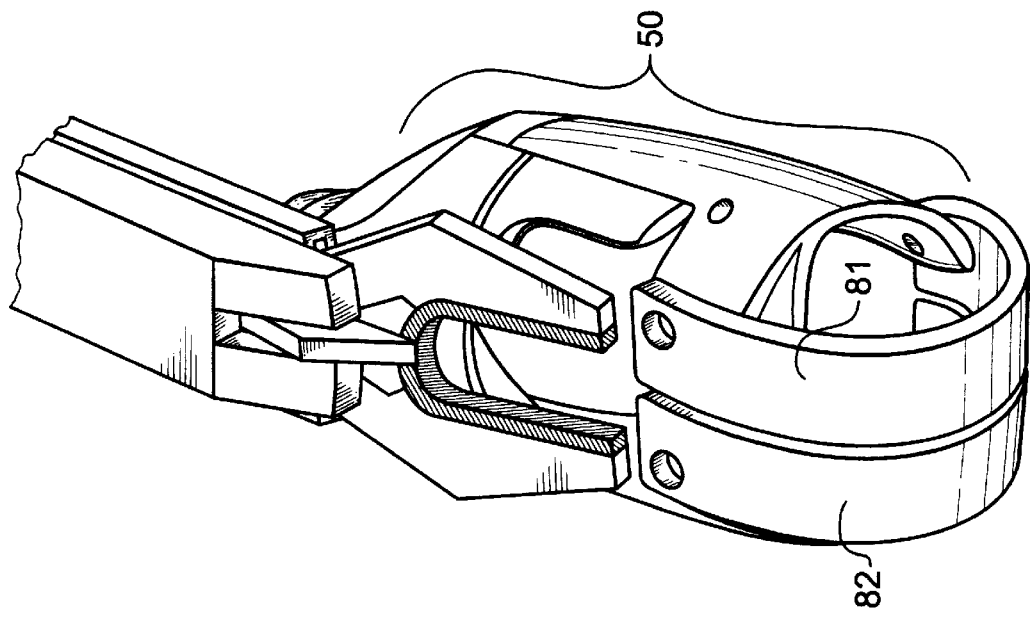
FIGS. 11A–B are the integrated vessel harvesting assembly having a transverse cutting mechanism to sever a major vessel and is preferably attached to the most distal portion of the integrated assembly of FIGS. 8, 9, and 10.
Figure 11A:
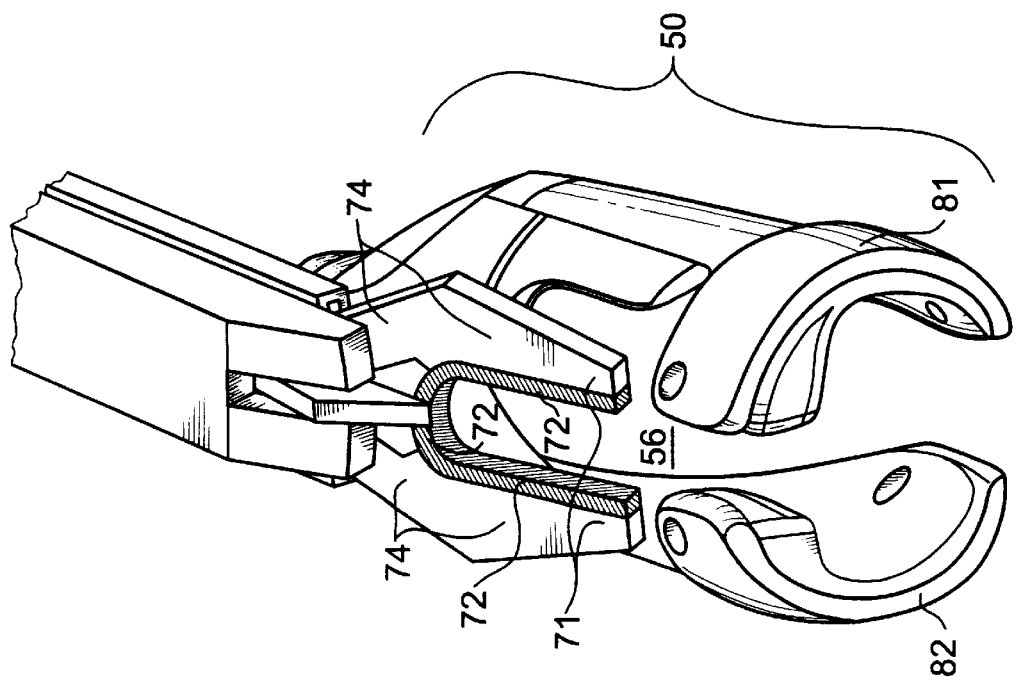
Figure 12D:
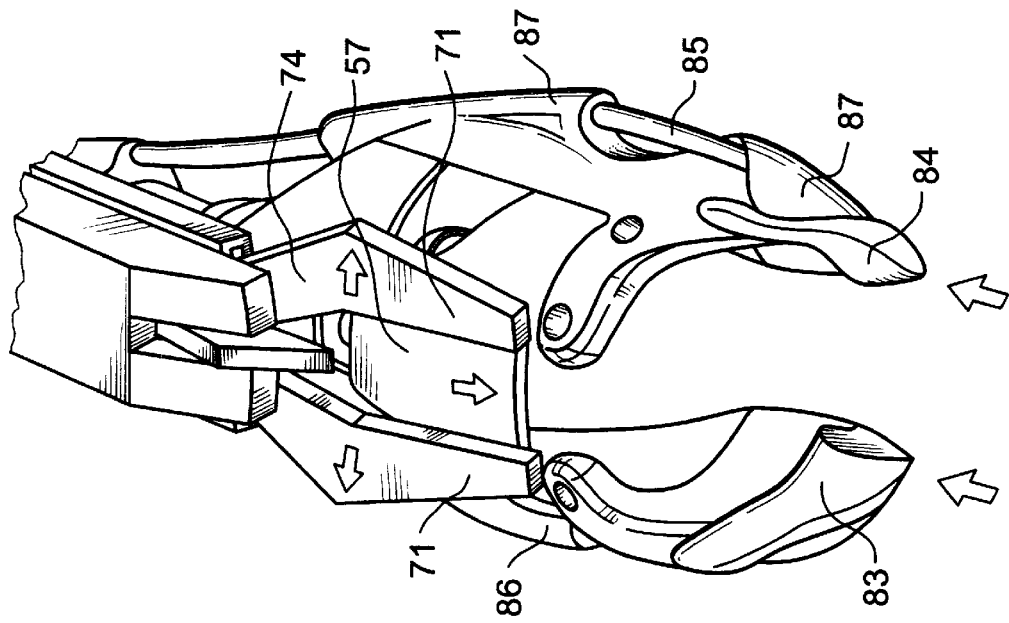
Figure 12C:
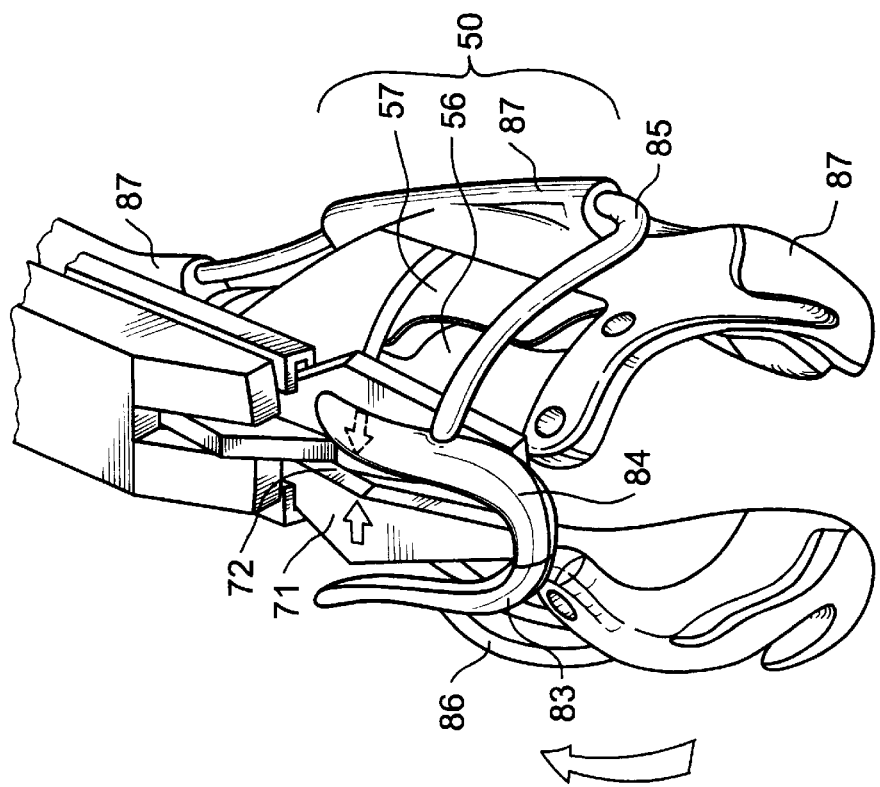

Referring to FIGS. 11A–B, the integrated assembly 50 may also include a transverse cutting mechanism for severing the major vessel, and which is located at the distal tip of the assembly 50. The cutting mechanism should operate in a transverse fashion, i.e., perpendicular to the linear path of the major vessel so that the entire vessel can be severed by the cutting mechanism. The transverse cutting mechanism may be provided by cutting members 81, 82 which are shaped to be concentric to the body of the assembly 50 thus allowing the cutting members 81, 82 to remain in a retracted position during the harvesting procedure. A suitable positioning of the cutting members 81, 82 may be achieved by affixing each member to the body 55 of the assembly 50 at a point or points to provide an axis of rotation A—A for each member 81 and 82 through the body 55 of the assembly such that the members can be rotated from their retracted position, concentric to the body 55 of the assembly, to engage one another (FIG. 11B) at their most distal surfaces to sever the major vessel positioned within the guide portion 59 of the body 55 of the assembly 50. As with the other cutting mechanisms disclosed herein, the cutting action may be enhanced, if desired, by providing bipolar electrodes at surfaces of the respective members 81, 82.

Referring to FIGS. 12A–12D, the need for a separate cutting mechanism at the distal end of the assembly 50 may be eliminated by providing the integrated vessel harvesting assembly with means for positioning the major vessel such that the major vessel itself may be separated, clipped, or severed by the same mechanism of the integrated assembly 50 used to separate the side branches of the vessel. The major vessel may be positioned by a pair of vessel guides 83, 84 disposed at the distal end of the integrated assembly 50. Each guide 83, 84 is actuated by a push rod 85, 86 formed of a memory metal which may be directed by one or more wire guides 87 and which, when extended, causes the vessel guides 83, 84 to join together into a unitary structure supporting the underside of the vessel. As the push rods 85, 86 are further extended, the memory shape of the push rods 85, 86 lifts the joined vessel guides to redirect a portion of the vessel to a position substantially approaching a 90° angle to the remaining portions of the vessel. In this position, the portion of the vessel thus guided into a position within aperture 56 of the integrated assembly 50, may have a clip 72 applied by plier mechanism 74, or may be severed by the movable blade member 57.

The particular examples set forth herein are instructional and should not be interpreted as limitations on the applications to which those of ordinary skill are able to apply this invention. Modification and other uses are available to those skilled in the art which are encompassed within the spirit of the invention as defined by the scope of the following claims.

We claim:

1. An integrated vessel harvesting assembly comprising:
    a body having an annular portion and at least two openings therein,
    wherein at least one opening leads to an aperture formed in a circumferential surface of the body and a second opening completely traverses said body, said second opening adapted to provide a guide portion for a vessel disposed within said body,
    a blade member movably coupled to said body proximate to said aperture said blade member adapted to sever a side vessel disposed within said aperture, and
    means for positioning and rotating said assembly.

2. The integrated assembly of claim 1 wherein the means for positioning and rotating the assembly and the means for actuating said movable blade member are co-axial.

3. The integrated assembly of claim 1 further comprising an integrally formed clip applier comprised of a plier mechanism positioned proximate to said aperture.

4. The integrated assembly of claim 3 further comprising at least one vessel guide proximate to said opening traversing the body and attached to means for actuating said vessel guide, wherein said vessel guide is movable relative to said opening.

5. The integrated assembly of claim 1 wherein said blade member is positioned transverse a longitudinal axis of said annual portion.

6. The integrated assembly of claim 5 wherein said blade member has an axis of rotation substantially perpendicular to a longitudinal axis of said annular portion.

7. The integrated assembly of claim 1 wherein said blade member is moveable relative to an edge of the aperture and said blade member and said edge of the aperture cooperate to provide a cutting structure adapted to sever a side vessel disposed within said aperture.

8. The integrated assembly of claim 7 wherein said moveable blade member and said body are bipolar.

9. The integrated assembly of claim 7 further comprising means for actuating said movable blade member.

10. A method for minimally invasive harvesting of the saphenous vein comprising:
    placing the saphenous vein within the body of an integrated vessel harvesting assembly by passing the vein through a first opening in the body thereof,
    advancing the integrated assembly along a length of the saphenous vein while rotating the assembly, and
    separating side vessels of the saphenous vein by rotating the assembly to pass the side vessels through a second opening in the body thereof and into an aperture formed in a circumferential surface of the body and actuating a movable blade member to engage the side vessels between said blade member and an edge of said aperture.

11. The method of claim 10 wherein the side vessels are separated from the saphenous vein by electrocautery.

12. The method of claim 10 further comprising severing the saphenous vein at the distal end thereof by positioning the saphenous vein within said aperture in the body.

13. The method of claim 12 wherein the saphenous vein is positioned by vessel guides extending from the distal end of the assembly.

14. A method for minimally invasive harvesting of the saphenous vein comprising:
    placing the saphenous vein within the body of an integrated vessel harvesting assembly by passing the vein through a first opening in the body thereof,
    advancing the integrated assembly along a length of the saphenous vein while rotating the assembly,
    separating a side vessel of the saphenous vein by applying a surgical clip to the side vessel,
    rotating the assembly to pass the side vessels through a second opening in the body thereof and into an aperture formed therein, and
    actuating a movable blade member to engage the side vessel.

15. The method of claim 14 wherein the surgical clip is applied with a clip applier which is attached to the integrated assembly.

* * * * *